United States Patent
Dhanaraj et al.

(10) Patent No.: US 8,071,137 B2
(45) Date of Patent: Dec. 6, 2011

(54) METHOD FOR TREATMENT OF CARTILAGE DISORDERS WITH CENTELLA EXTRACT

(75) Inventors: Sridevi Dhanaraj, Raritan, NJ (US); Carrie H. Fang, Pittstown, NJ (US)

(73) Assignee: Advanced Technologies and Regenerative Medicine, LLC, Raynham, MA (US)

( * ) Notice: Subject to any disclaimer, the term of this patent is extended or adjusted under 35 U.S.C. 154(b) by 476 days.

(21) Appl. No.: 12/059,915

(22) Filed: Mar. 31, 2008

(65) Prior Publication Data

US 2008/0226754 A1 Sep. 18, 2008

Related U.S. Application Data

(62) Division of application No. 11/235,850, filed on Sep. 27, 2005.

(51) Int. Cl.
*A61K 36/00* (2006.01)

(52) U.S. Cl. .................................................. 424/725

(58) Field of Classification Search .................. None
See application file for complete search history.

(56) References Cited

U.S. PATENT DOCUMENTS

| | | | | |
|---|---|---|---|---|
| 4,675,183 A * | 6/1987 | Kato et al. | | 424/85.4 |
| 6,228,387 B1 | 5/2001 | Borod | | |
| 6,417,349 B1 | 7/2002 | Kim et al. | | |
| 6,579,543 B1 | 6/2003 | McClung | | |
| 2002/0076452 A1 * | 6/2002 | Babish et al. | | 424/725 |
| 2002/0197336 A1 | 12/2002 | Mini et al. | | |
| 2003/0134792 A1 * | 7/2003 | Pike et al. | | 514/12 |
| 2005/0089500 A1 * | 4/2005 | Pinnell | | 424/74 |

FOREIGN PATENT DOCUMENTS

| | | |
|---|---|---|
| BE | 874751 A | 7/1979 |
| GB | 2 049 416 A | 12/1980 |
| JP | 06312931 * | 11/1994 |
| WO | 01/19365 A1 | 3/2001 |

OTHER PUBLICATIONS

Philipson. New Drugs From Nature—It Could be Yew. Phytotherapy Research. 13, 1999, pp. 2-8.*
Revilla et al. Comparison of Several Procedures Used for the Extraction of Anthocyanins From Red Grapes. J. Agric. Food Chem. 1998, 46, pp. 4592-4597.*
Zheng et al. Chemical Components of *Centella asiatica* and Their Bioactivities. Journal of Chinese Integrative medicine. May 2007. vol. 5, No. 3. 248-351.*
Hans J. Haeuselmann et al.; "Phenotypic Stability of Bovine Articular Chondrocytes After Long-Term Culture in Alginate Beads"; Journal of Cell Science 107; pp. 17-27, (1994.
Karin Scharffetter, M.D. et al; "Localization of Collagen α1 (I) Gene Expression During Wound Healing by in Situ Hybridization"; The Journal of Investigative Dermatology; pp. 405-412, (1989).
Noushin S. Dunkelman, et al.; "Cartilage Production by Rabbit Articular Chondrocytes on Polyglycolic Acid Scaffolds in a Closed Bioreactor System"; Biotechnology and Bioengineering, vol. 46,; pp. 299-305; (1995).
David G. Stokes, et al.; "Regulation of Type-II Collagen Gene Expression During Human Chondrocyte De-Differentiation and Recovery of Chondrocyte-Specific Phenotype in Culture Involves Sry-type High-Mobility-Group Box (SOX) Transcription Factors"; Biochemical Society; pp. 461-470; (2001).
R. Lane Smith, M.C.D., et al.; "Effects of Shear Stress on Articular Chondrocyte Metabolism"; Biorheology 37, IOS Press; pp. 95-107; (2000).
Abstract Only—[Dermis Collagens: beyond their structural properties].

* cited by examiner

*Primary Examiner* — Melenie McCormick
(74) *Attorney, Agent, or Firm* — Roberts Mlotkowski Safran & Cole, P.C.

(57) ABSTRACT

The invention is a method for the treatment of mammalian articular cartilage disorders, inflammatory joint disease, trauma-related cartilage injuries, and degenerative disc disease. The method involves treating the affected area with a composition containing a therapeutically effective dose of *Centella* extract. The composition is delivered locally by parenteral administration to the affected site.

12 Claims, No Drawings

METHOD FOR TREATMENT OF CARTILAGE DISORDERS WITH CENTELLA EXTRACT

This application is a division of co-pending U.S. patent application Ser. No.11/235,850, filed Sep. 27, 2005, the contents of which are incorporated by reference in their entirety.

FIELD OF THE INVENTION

The invention is directed toward the treatment of mammalian articular cartilage disorders, inflammatory joint disease, trauma-related cartilage injuries, degenerative disc disease, and for treatment following arthroplastic surgery. More specifically, the invention relates to a composition containing an effective dose of *Centella* extract.

BACKGROUND OF THE INVENTION

Articular cartilage plays an essential role in the movement of mammalian joints. It provides a superior smooth surface between adjacent bones, allowing for near-frictionless motion of joints. Synovial fluid within the joint cavity serves as a lubricant. It is the articular cartilage that spreads compressive stresses over the articular plate surfaces of the joint, thus protecting weight-bearing bones from shattering or deteriorating.

Articular cartilage is composed of chondrocytes embedded in an extracellular matrix of proteoglycans, collagen, and small molecular weight glycoproteins. Chondrocytes are cartilage cells embedded in lacunae within the cartilage matrix. Proteoglycans are essential in maintaining strength of the cartilage tissue so that it can withstand compression. Collagen provides the tissue with tensile strength and resistance to shear. In a healthy joint, the extracellular matrix is maintained by a balance between the synthesis and secretion of these macromolecules by chondrocytes and their subsequent degradation by proteolytic enzymes such as proteoglycanases and metalloproteinases, which are also synthesized and secreted by chondrocytes. Damage to the cartilage of the articular surface can disrupt this equilibrium, such that degradation exceeds the ability of chondrocytes to synthesize macromolecules necessary for repair of the cartilage tissues. Chronic disruption of the equilibrium between synthesis and degradation of cartilage matrix macromolecules is associated with the development of osteoarthritis.

Osteoarthritis (OA), also known as degenerative joint disease, is the most common form of arthritis and results from the gradual breakdown of cartilage that accompanies aging. Typically, OA follows trauma or chronic joint injury due to some other type of arthritis such as rheumatoid arthritis. Alternatively, OA can result from overuse of a particular joint. OA may be classified as: primary, in which no underlying cause is apparent; secondary, which is associated with a predisposing factor such as trauma, repetitive stress (occupation, sports), congenital abnormality, metabolic disorder, or other bone/joint disease; and erosive, a syndrome characterized by periods of acute inflammation and progressive destruction of the joints occurring most often in middle-aged women. OA most is most commonly prevalent in the joints of the fingers, hips, knees, spine, base of the thumb, and big toe. Clinically, OA is characterized by joint pain, tenderness, and limitation of movement, crepitus, and inexorably progressive disability. It can be present in just one of these joints or in all of them. Although most body tissues can make repairs following an injury, cartilage self-repair is hampered by a limited blood supply and the lack of an effective mechanism for cartilage re-growth.

In osteoarthritis, the first alteration in the joint, which takes place over decades, is a roughening of articular cartilage followed by pitting, ulceration, and progressive loss of cartilage surface. Proinflammatory cytokines accelerate degradation of the cartilage matrix. Persistent inflammation produces symptoms and damages tissue resulting in loss of cartilage, erosion of bone matter, and subluxation of the joint. There is compelling evidence that soluble inflammatory mediators (i.e., molecules that are released by immune cells during times when harmful agents invade our body) such as cytokines, interleukin-1 (IL-1) and tumor necrosis factor-a (TNF-a), are involved in the osteoarthritis process. By inducing the synthesis of proteolytic enzymes, cytokines interfere with the action of growth factors such as the insulin growth factor-I (IGF-1) binding proteins. Moreover, the inflammatory cytokines have the ability to suppress the synthesis of type II collagen, characteristic of hyaline cartilage, while augmenting the synthesis of type I collagen, characteristic of fibroblast cells. In addition, IL-1 reduces aggrecan synthesis, the macromolecule largely responsible for the mechanical properties of articular cartilage.

Historically, treatment of osteoarthritis and articular cartilage injuries has been limited to pain relief, reduction of joint loading, physical therapy, and orthopedic surgery, all of which are aimed at symptomatic relief rather than treatment of the underlying pathologic disorder. More recently, osteoarthritis research has concentrated on development of chondroprotective methods. Such methods involve long-term therapeutic treatment aimed at preserving or stimulating cartilage formation. Present treatment of arthritis includes first line drugs for control of pain and inflammation classified as non-steroidal anti-inflammatory drugs (NSAIDs), such as, aspirin, ibuprofen, naproxen, and methotrexate. Secondary treatments include corticosteroids, slow acting anti-rheumatic drugs (SAARDs) or disease modifying drugs (DMs), such as, pencillinamine, cyclophosphamide, gold salts, azothipprine, and levamisole. Although NSAIDS are one of the major groups of drugs in terms of sales and use for the management of OA among the general population, their side effects have become an issue in the risk/benefit determination, particularly in the elderly. Depending upon individual circumstances, NSAIDS may cause gastrointestinal hemorrhage, ulceration, or perforation, while some are associated with bone marrow depression, several cause fluid retention, and may contribute to renal failure. These effects are particularly important because such treatments are often long-term. While the previously mentioned drugs have met with some degree of success in the preventative treatment of osteoarthritis, new and improved methods and pharmaceutical compositions are constantly being sought which may effectively reduce the progression of lesion and cartilage degradation in a mammal suffering from osteoarthritis. It is therefore an object of the present invention to provide a methodology for effectively treating arthritis, degenerative disc disease, and cartilage diseases.

Herbal medicines for treatment of a variety of ailments in mammals are known. Typically, such herbal medicines are obtained as the active compound(s) by extraction from plant tissues. For example, it is known to treat degenerative musculoskeletal diseases such as rheumatoid arthritis and osteoarthritis in an animal, typically a human, by enteric administration of a therapeutically effective amount of the beneficiated extracts of the plants *Withania somnifera, Boswellia serrata, Curcuma longa*, and *Zingiber officinale* in a predetermined proportion to each other. It is also known to treat inflammation in a patient by oral administration of an effective dose of a pharmaceutical composition containing essential oils extracted from tissues of *Curcuma domestica*, or *Curcuma xanthorrhiza*, or both oils and curcuminoid substantially free of bis-desmethoxycurcumin. Edible herbal compositions containing a mixture of at least three, and as many as seven, herbs selected from *Tanacetum parthenium, Zingibar officinale, Curcuma longa, Coriandrum sativum, Centella asiatica, Oenothera biennis, Valeriana officinalis*, have been used as anti-inflammatory agents for alleviation of arthritis and gout is also known It is also known that acetylglucosamine and the individual compound glucuronic acid can be combined with plant extracts selected from the group consisting of *Vaccinum Myrtillus, Sylibum Marianum, Echinacea Angustifolia, Aesculus Hippocastanum, Calendula Officinalis, Centella Asiatica, Hamamelis Virginiana, Citrus Aurantium Amara, Citrus Aurantium Dulcis, Citrus Limonium, Equisetum Arvense, Glycyrritia Glabbra, Aloe Vera, Ruta Graveolans, Vitis Vinifera* and *Terminalia Sericea* for cosmetic, pharmaceutic and dietic use. Also, it is known that COX-2 can be inhibited using an organic extract isolated from edible plants.

Although the use of various herbs has been described in related areas, the use of a parenteral composition of *Centella* extract for the treatment of osteoarthritis, cartilage injury, and degenerative disc disease has never previously been described.

The plant *Centella Asiatica* can be found throughout Asia and is commonly employed in skin disease. Reports to support these properties have been published as early as in 1971. The three active components of *Centella* extract, asiaticoside, asiatic acid, and madecassic acid, were also identified and tested. The specific role that each of these component compounds plays in the biological activity of *Centella* however, is unknown. The crude extract as well as the active components were claimed to be effective not only in the treatment of leprosy, but also in slow-healing wounds, surgical lesions, phlebitis, and leg ulcers (Lille Med, 1971, 17:Suppl 3:574-9). The active components as well as the crude extracts have been reported to increase collagen synthesis and cellular proliferation (Contact Dermatitis, 1993, 39(4): 175-9; Eur J Dermatol, 1999, 9(4): 289-96; Ital J Biochem, 1988, 37(2), 69-77). They also enhanced the rate of dermal wound healing in rats (Indian J. Exp. Boil, 1996, 34(12): 1208-11). In clinical studies, extracts from *Centella* have been claimed to be beneficial in preventing as well as reducing scarring (Bossee J P, et al: Clinical Study of a new anti-keloid agent). One important feature that could make *Centella* extracts attractive for use in wound healing treatment is that repeated applications on damaged skin did not lead to development of contact sensitivity (Lille Med, 1971, 17:Suppl 3:574-9). Numerous studies have elucidated the wound healing and anti-scarring properties of *Centella*. Isolated extracts of this plant have been used orally to treat migraines, arthritis, and bronchial complaints. There are no reports discussing the use of a parenteral composition of *Centella* extract for treatment of arthritis and other cartilage and disc related disease.

There is a constant need in this art for new compositions for treating arthritis and cartilage degeneration, as well as new methods of treating such conditions.

SUMMARY OF THE INVENTION

Accordingly, a novel, parenteral pharmaceutical composition for treating mammalian articular cartilage disorders is disclosed. The parenteral composition consists of an extract of *Centella* and a pharmaceutically acceptable carrier.

Another aspect of the present invention is a novel method for the treatment of mammalian articular cartilage disorders is disclosed. In the method of the present invention, a therapeutically effective amount of parenteral composition containing *Centella* extract and a pharmaceutically acceptable carrier is administered to an affected site having mammalian articular cartilage disorder.

These and other aspects and advantages of the present invention will become more apparent from the following description and examples.

DETAILED DESCRIPTION OF THE INVENTION

The invention provides a parenteral composition containing *Centella* extract useful for reducing pain, inflammation, or stiffness associated with inflammatory conditions such as arthritis, inflammatory joint disease, degenerative disc disease, articular cartilage disorders, and osteoarthritis and the like, and preventing progression of the disease. Reducing pain, inflammation, or stiffness associated with an inflammatory condition is believed to be helpful in improving joint mobility. In addition, the compositions and methods of the invention provide a safe and effective treatment utilizing natural ingredients.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In addition, the materials, methods, and examples are illustrative only and not intended to be limiting. Extract means crude extract, purified extract, and purified composition obtained by purification of the extract. Purified means partially purified or completely purified. Thus, a purified composition may be either partially purified or completely purified.

The novel compositions and methods of the present invention provide effective prophylactic or curative pharmacological treatment of an inflamed joint for the relief of pain and prevention of joint damage in a warm-blooded animal including man. These compositions and methods additionally provide such treatment for patients having medically critical conditions such as patients suffering from acute arthritic inflammation and pain, physical trauma, within or in close proximity to the joint, and also provide a vehicle for other pharmacologically active drugs such as anti-inflammatory, antibiotic, anti-viral, anesthetic, cytostatic, and disease modifying agents.

These aspects of the present invention, and others set forth more fully herein below are achieved by methods for treating inflammatory joint disorder in a mammal in need of such treatment, which consist of injecting into the joint of the mammal a therapeutically effective amount of a novel composition of the present invention consisting of a pharmaceutically acceptable parenteral composition having clinical grade *centella* extract in combination with suitable diluents or carriers.

The compositions and methods of the present invention may be used exclusive of, or as an adjunct to, anti-inflammatory agents, analgesic agents, muscle relaxants anti-depressants, or agents that promote joint lubrication commonly used to treat disorders associated with joint stiffness such as arthritis. A combined therapeutic approach may be beneficial in reducing side effects associated with agents, such as non-steroidal anti-inflammatory drugs (NSAIDs), commonly used to present, manage, or treat disorders such as OA associated with reduced joint lubrication. In addition to enhancing safety, a combined therapeutic approach is also advantageous in increasing efficacy of treatment.

*Centella* extract is a mixture of compounds isolated from a plant from the Hydrocotyl genus (hereinafter referred to as *Centella*). Examples of *Centella* include, but are not limited to, *Centella Asiatica*, or *Centella Erecta*, as well as those listed in CRC Ethnobotany Desk Reference 1998 and the International Plant Names Index. *Centella* extracts may be isolated from the plant tissues (e.g., the arial part of the plant such as the stem, flower, and leaves) by physically removing a piece of the plant, followed by grinding. Such compounds may also be isolated from the plant by using extraction procedures well known in the art. For example, organic solvents such as $C_1$-$C_8$ alcohols, $C_1$-$C_8$ alkyl polyols, $C_1$-$C_8$ alkyl ketones, $C_1$-$C_8$ alkyl ethers, acetic acid $C_1$-$C_8$ alkyl esters, and chloroform, or inorganic solvents such as water, inorganic acids such as hydrochloric acid, and inorganic bases such as sodium hydroxide may be used as extraction solvents. In one embodiment, the *Centella* extract contains only hydrophilic compounds isolated by using a hydrophilic solvent, such as water or ethanol. In another embodiment, the *Centella* extract contains only hydrophobic compounds isolated by using a hydrophobic solvent, such as chloroform. In yet another embodiment, the *Centella* extract contains both hydrophilic and hydrophobic compounds. In addition to extracting the *Centella* from plant tissues, the *Centella* extract can be obtained from a commercial vendor such as Roche Nicholas Laboratories S.A. (Gaillard, France). The amount of the *Centella* extract present in the composition will depend upon the type of extract used. In a preferred embodiment, the composition of the present invention consists of a safe and therapeutically effective amount of said *Centella* extract in a pharmaceutically acceptable carrier. The extract typically will be present in the composition in an amount between about 0.001% to about 20% by weight, preferably in an amount between about 0.01% to about 1% by weight. The *Centella* extract may contain asiatic acid, madecassic acid, asiaticoside, and triterpenes. Asiatic acid, madecassic acid, asiaticoside and triterpenes may be present in the composition between about 0.001% to about 0.5% by weight, preferably between about 0.005% and 0.2% by weight of the composition.

The anti-inflammatory activity of the extracts may be assessed by employing enzyme linked immuno sorbent assay (ELISA) procedures generally known to those skilled in the art. The relative ability of various *Centella* extracts to inhibit inflammatory cytokines at a particular concentration may be determined by comparing the $IC_{50}$ value expressed as micrograms extract/milliliter solvent resulting in a 50% inhibition of inflammatory cytokine. Additionally, any other means to determine inhibition of inflammatory activity known to those generally skilled in the art may be employed.

Those of ordinary skill in the art of preparing parenteral pharmaceutical formulations can readily formulate pharmaceutical compositions having *Centella* extracts using a known pharmaceutically acceptable carrier. Pharmaceutically acceptable carrier means a carrier that is conventionally used in the art to facilitate the storage, administration, or the healing effect of the therapeutic ingredients. In addition, those of ordinary skill in the art can readily determine appropriate dosages that are necessary to achieve the desired therapeutic, prophylactic, pathologic, or resuscitative effect upon parenteral administration to the organism. Typically, in vivo models using laboratory mammals are used to determine the appropriate plasma concentrations necessary to achieve a desired mitigation of inflammation related conditions.

In the practice of the present invention, additional factors should be taken into consideration when determining the therapeutically effective dose of *Centella* extract and the frequency of its administration. Such factors include, for example, the size of the joint, the area of the surface of the cartilage affected, the severity of the cartilage injury or osteoarthritis, and the age, height, weight, health, and physical condition of the individual to be treated. Generally, a higher dosage is preferred if the joint is larger or the disorder or injury is more severe. Some minor degree of experimentation may be required to determine the most effective dose and frequency of dose administration, and is well within the capability of one skilled in the art once apprised of the present disclosure.

The composition may be formulated with *Centella* extract as the sole pharmaceutically active ingredient or may be formulated with other active ingredients in a pharmaceutically acceptable carrier. A suitable carrier should be stable and incapable of reacting with other ingredients in the formulation. It should not produce significant local or systemic adverse effect in recipients at the dosages and concentrations employed for treatment. Such carriers are generally known in the art. Representative and non-limiting examples for this invention are a sterile diluent, such as water for injection or saline solution, large stable macromolecules such as albumin, gelatin, collagen, polysaccharide, monosaccarides, polyvinylpyrrolidone, polylactic acid, polyglycolic acid, and polymeric amino acids, fixed oils, ethyl oleate, liposomes, glucose, sucrose, lactose, mannose, dextrose, dextran, cellulose, mannitol, sorbitol, polyethylene glycol (PEG), isopropyl alcohol, gaseous fluorocarbons, ethyl alcohol, polyvinyl pyrrolidone, propylene glycol, glycerine, a gel-producing material, stearyl alcohol, stearic acid, spermaceti, sorbitan monooleate, methylcellulose and the like.

Slow or controlled release vehicles may also be pharmaceutically acceptable carriers. Examples of slow or controlled release vehicles are liposomal suspensions and colloidal dispersion systems. Liposomes are artificial membrane vesicles, which are useful as slow release delivery vehicles when injected or implanted. These may be prepared according to methods known to those skilled in the art. Useful colloidal dispersion systems include nanocapsules, microspheres, beads, and lipid-based systems, including oil-in-water emulsions, micelles, mixed micelles, and liposomes. The colloidal system presently preferred is a liposome or microsphere. Other examples of slow release delivery vehicles are biodegradable hydrogel matrices, dendritic polymer conjugates, hyaluronic acid, and multivesicular liposomes. One type of microspheres suitable for encapsulating therapeutic agents for local injection (e.g., into subdermal tissue) is poly (D, L)-lactide microspheres. The compositions described herein can be supplied in a suitable, conventional dosage form including ampoules, disposable syringes or multiple dose vials made of glass, plastic or other suitable biocompatible material, intravenous pouches, etc. The compositions of the present invention may additionally include a solubilizing compound. A solubilizing compound is capable of enhancing the solubility of the *Centella* extract, such as a compound that has a guanidinium group. Examples of such solubilizing compounds include the amino acid arginine, as well as amino acid analogs of arginine that retain the ability to enhance solubility of *Centella* extract at physiological pH. Such analogues include, without limitation, dipeptides and tripeptides that contain arginine. The solubilizing compound of the present invention may also include, alone or in combination, substances belonging to the chemical class of amino acids selected from the group consisting of alanine, arginine, aspartic acid, asparagine, cysteine, glutamic acid, glutamine, glycine, histidine, leucine, isoleucine, lysine, methionine, phenylalanine, proline, serine, threonine, tryptophan, tyrosine, valine, the corresponding salts and esters and the various forms reduced to amino alcohols, both in dextrorotatory and levorotatory form and the related racemic mixtures.

The compositions of the present invention may further include a synergist compound. A synergyst may enhance the therapeutic effect of the *Centella* extracts. Synergists include compounds such as acetylglucosamine or glucuronic acid.

It is also advantageous to administer the compositions of the present invention together with other pharmaceutically active compounds such as an analgesic or other pain reducing medication, anti-inflammatory compounds, muscle relaxants, anti-depressants, antibiotics, anti-viral, anesthetic, cytostatic, and other disease modifying agents. Suitable analgesics or pain reducing compounds include acetaminophen and ibuprofen. Other anti-inflammatory compounds include non-steroidal anti-inflammatory drugs (NSAIDs), prostaglandins, such as choline magnesium salicylate and salicyclic acid, and corticosteroids, such as methylprednisone, prednisone, and cortisone.

The compositions of the present invention may also contain agents that promote joint lubrication commonly used to treat disorders associated with joint stiffness such as viscosupplements. Viscosupplements increase the viscosity or visco-elasticity of the synovial fluid thereby reducing pain and discomfort in the affected area. Viscosupplements include, but are not limited to compounds such as carboxymethyl cellulose (CMC), hyaluronic acid, and glycosaminoglycans (GAGs), such as chondroitin sulphate.

The compositions of the present invention can additionally include anti-microbial agents, such as benzalkonium chloride, methyl- or propyl-paraben, and chlorobutanol; antioxidants, such as ascorbic acid sodium sulfite and sodium bisulfite; chelating agents, such as ethylenediaminetetraacetic acid (EDTA); buffers, such as acetates, citrates, succinates and phosphates; protease inhibitors, such as sodium pentosan polysulfate (PPS), a polysulfated polysaccharide; acetic acid, and other organic acids or their salts.

The compositions of the present invention for use in the methods for treatment described herein can be administered by any parenteral route known to those of skill in the art. Parenteral routes include but are not limited to, intra-articularly, intracistemally, intraocularly, intraventricularly, intrathecally, intravenously, intramuscularly, intra-peritoneally, intradermally, intratracheally, as well as by any combination of any two or more thereof. The most suitable route for administration will vary depending upon the disease state to be treated, for example the location of the inflammatory condition.

In one embodiment of the present invention, the method of administration of the therapeutically effective dose of composition of the present invention will result in localized delivery of *Centella* extract to the area of the affected joint. In this embodiment, the therapeutically effective dose of *Centella* extract is administered intra-articularly to the mammal needing treatment. Intra-articularly means direct administration into the cavity enclosing the movable joint having osteoarthritis or other cartilage injuries, so that substantial direct contact between the administered composition containing *Centella* extract and articular cartilage is achieved. Parenteral administration (intravenous or intra-articular) is often preferred in instances where rapid alleviation of patient distress is required. Another method of administration of the active compound to the synovial tissues of the subject involves intra-articular injection of the active compound, such that a therapeutically effective amount of the compound reaches the synovial tissues locally. Local administration, delivering an effective therapeutic dose to the affected site, decreases the chance of systemic toxicity, and decreases the exposure of the therapeutic agents to degradative processes, such as proteolytic degradation and immunological intervention via antigenic and immunogenic responses.

In another embodiment of the present invention, the administration of the therapeutically effective dose of the compositions of the present invention containing *Centella* extract is administered intra-articularly intermittently. Intermittent administration means the administration of a therapeutically effective dose the composition containing *Centella* extract, followed by a time period of discontinuance, followed by another administration of a therapeutically effective dose, and so forth. Administration of the therapeutically effective dose may be achieved in a continuous manner, as for example with a sustained-release formulation, or it may be achieved according to a desired daily dosage regimen, as for example with one, two, three or more injections per day. Time period of discontinuance means a discontinuing of the continuous sustained-released or daily administration of *Centella* extract. The time period of discontinuance may be longer or shorter than the period of continuous sustained-release or daily administration. An intermittent schedule of administration of the composition of the present invention containing *Centella* extract to the diseased or injured joint may continue until the desired therapeutic effect of maintenance or regeneration of cartilage, and ultimately treatment of the disorder or injury, is achieved.

The efficacy of a particular dose of the compositions of the present invention containing *Centella* extract e for any particular means of administration, including intra-articular injection, release at the site from a sustained release device or delivery system, and systemic injection, may be measured in accordance with the ability to promote the desired positive effect of maintenance or regeneration of cartilage within the diseased or injured joint, and ultimately treatment of the articular cartilage disorder or trauma-related injury. For example, efficacy of a particular dosage and dosing schedule, or regimen, for treatment of a disease such as osteoarthritis may be measured based on several variables, including, but not limited to, ability to improve pain or function within the diseased joint, to slow structural deterioration within the diseased joint, or to delay time to surgical replacement of the diseased tissue. Pain may be measured with any validated pain scale, such as a Likert scale, more preferably an IOcm VAS measurement. Improvement in an afflicted joint may be measured with any validated knee or hip osteoarthritis function measurement, such as that obtained with the Lequesne knee and hip instruments and with the WOMAC. Structural improvements may be validated with a comparison of baseline and final radiographic scores for joint space narrowing (JSN), such as JSN of an osteoarthritic knee or hip.

The compositions of this invention may be used to manage, prevent or treat an organism having, or at risk for developing, a condition which is mediated in whole or in part by inflammatory cytokines. Accordingly, conditions which may be benefited by inhibition of inflammatory activity but are not limited to, the treatment of inflammation in an organism, and for treatment of other inflammation-associated disorders, such as, arthritis, including but not limited to rheumatoid arthritis, spondyloarthopathies, gouty arthritis, osteoarthritis, systemic lupus erythematosus and juvenile arthritis, Reiter's syndrome, reactive arthritis, psoriatic arthritis, spondylitis, undifferentiated spondylarthopathies and Behcet's syndrome. The compositions of the present invention may be employed for the treatment or prevention of inflammation-related disorders, as identified above, in a number of organisms. Besides being useful for human treatment, these compositions are also useful for veterinary treatment of companion animals, and farm animals, including mammals, rodents, avians, and the like. More preferred animals include horses, dogs, cats, sheep, and pigs.

The compositions and methods of the present invention should be generally applicable to osteoarthritis caused by or associated with all of the above disorders. The compositions and methods of the present invention are also effective for treatment of degenerative disk disease, whereby cartilagenous tissue in the intervertebral disks breaks down. Osteoarthritis and degenerative disk disease are common causes of sustained back pain, and hence the method of the invention provides a means for alleviating this symptom by treatment of the underlying cause.

It will be apparent to those skilled in the art that the compositions and methods of the present invention can also be used in the treatment of trauma-related articular cartilage injuries, via the same mechanism as for osteoarthritis, by promoting maintenance or regeneration of cartilage. Trauma-related articular cartilage injuries is defined as damage caused to the chondrocytes, extracellular matrix, or other components of articular cartilage as a result of a traumatic event such that normal joint movement is impaired or is at risk of being adversely affected. Such injuries can be either acute or chronic, and include occupation-related, accident-related, sports-related, or violence-related injuries. When left untreated, serious articular cartilage injuries can eventually lead to development of osteoarthritis.

Treatment is defined as both therapeutic treatment of an existing articular cartilage disorder, more particularly osteoarthritis, or trauma-related articular cartilage injury, degenerative disc disease, and preventive or prophylactic procedures performed before the occurrence of the disorder or injury. Thus, the mammal to be treated may already have the disorder or injury or may be prone to having the disorder or injury. Risk factors known to predispose an individual to osteoarthritis can be taken into account when determining whether preventive treatment is desirable. For example, it is generally known that the risk of osteoarthritis increases with age and repetitive stress, such as vocational-related stress. It also has been observed that individuals suffering from, obesity, congenital or developmental defects, metabolic or endocrine disorders, and prior inflammatory joint diseases are more prone to osteoarthritis. Thus, it may be desirable to apply the compositions and methods of the present invention for preventive purposes in these cases. The compositions and methods of the present invention may be used with any mammal. Exemplary mammals include, but are not limited to, cats, dogs, horses, cows, sheep, pigs, and more preferably humans.

The following examples are illustrative of the principles and practice of the present invention, although not limited thereto. Crude extracts of *Centella* obtained from a commercial source (Amsar Pvt. Ltd, Indore, India) (in a powder form) were dissolved in phosphate buffered saline (PBS) (Invitrogen, Carlsbad, Calif.) at the final concentration of 10%, and sterilized using a 0.2 micron filters and stored at 4° C. All dilutions of extracts were made in the respective culture medium. The following concentrations of *Centella* extracts were used for the experiments 1 and 10 and 100 micrograms/milliliter

EXAMPLE 1

Inhibition of IL-6 Production in Activated Mouse Macrophages by *Centella* Extract The effect of *Centella* extract on inhibition of production of IL-6 was analyzed using the Cytoscreen Immunoassay Kit (Biosource International (Camarillo, Calif.). Mouse macrophages (IC-21) were seeded at $5 \times 10^4$ cells/well in RPMI-1640 (Life Technologies (Frederick, Md.). containing 10% fetal bovine serum (FBS) (HyClone (Logan, Utah) in a Nunc, Inc. 96-well plate (Fisher Scientific, Pittsburgh, Pa.). Macrophages were activated by treatment with Lipopolysaccharide, LPS (Sigma Chemicals St. Louis, Mo.). (10 nanograms/milliliter) for 24 hours prior to treatment with extracts. Cells were then treated for 24 hours with extracts of *Centella*. Each treatment was performed in triplicate. The culture medium was harvested and IL-6 levels were analyzed by ELISA following manufacturer's instructions.

Table-1 shows IL-6 levels obtained upon treatment with *Centella* extract in comparison to the control sample without *Centella* extract.

TABLE 1

| Inhibition of IL-6 production by *Centella* extract | |
|---|---|
| *Centella* extract (micrograms/milliliter) | IL-6 (picograms/milliliter) |
| 0 | 1825 +/− 361 |
| 10 | 1700 +/− 80 |
| 100 | 1415 +/− 46 |

Results showed that *Centella* extracts at the concentration of 100 micrograms/milliliter suppressed the production of IL-6 indicating the potential of the extract to suppress inflammatory cytokine in the diseased joint. This reduction in IL-6 contributes, at least in part, to the mechanism whereby the *Centella* extract reduces Matrix metalloproteinases (MMP) synthesis in vivo.

EXAMPLE 2

Inhibition of Gag Release in Bovine Articular Cartilage Stimulated with IL-1betã

Three week old bovine alginate-recovered chondrocyte (ARC) tissue in 3 mm punches was purchased from Articular Engineering, Inc. (Chicago, Ill.). Punches were transferred into a 96 deep well plate (Nunc Inc., Fisher Scientific, Pittsburgh, Pa.), 1 punch per well. Punches were washed once with low serum DMEM medium (Life Technologies (Frederick, Md.). (1% FCS) supplemented with 10 micrograms/milliliter ITS (Sigma, St. Louis, Mo.) and treated with *Centella* extracts at 1 and 10 micrograms/milliliter at 37° C. 1 hr prior to addition of 7.5 nanograms/milliliter of IL-1 beta to stimulate matrix degradation and partly mimic the in vivo OA condition. The punches were further incubated at 37° C. for 5 days before the culture medium was analyzed for GAG release from the ARC into the medium. The media was evaluated for GAG content using the Dimethyl Methylene Blue (DMB) assay (Farndale, et.al., 1986).

Table-2 shows concentration of GAG release in relationship to concentration of *Centella* extract added to the well.

TABLE 2

Inhibition of GAG release in Bovine ARC stimulated with IL-1beta

| Centella extract (micrograms/milliliter) | GAG (micrograms/milliliter) |
|---|---|
| 0 | 44.13 +/− 4.93 |
| 1 | 42.0 +/− 3.15 |
| 10 | 33.09 +/− 1.35 |

Our findings provide evidence that the in vivo cartilage breakdown as assessed by GAG release in the ARC culture system can be mitigated by treatment with *Centella* extracts. Results demonstrated that *Centella* extracts inhibit the breakdown of the cartilage matrix from the ARC pellets as assessed by the decrease in GAG release in the medium, indicating the potential of the extract to suppress matrix loss in the diseased joint. This reduction in GAG release contributes, at least in part, to the mechanism whereby the *Centella* extract reduces and protects the joint from further damage.

EXAMPLE 3

Inhibition of Nitric Oxide (NO) production in Bovine Articular Cartilage stimulated with IL-1 beta Experiments were set up with bovine ARC as outlined in Example 2. At the end of culture the medium was analyzed for total nitrate and nitrite released as an index of total NO production. The media was evaluated for total nitrate and nitrite content using the Nitrate/Nitrite calorimetric assay kit from Cayman Chemical (Ann Arbor, Mich.).

Table-3 shows concentration of NO produced as a function of amount of *Centella* extract added to the culture medium.

TABLE 3

Inhibition of NO production in bovine ARC stimulated with IL-1beta

| Centella extract (micrograms/milliliter) | NO production (micromolar) |
|---|---|
| 0 | 11.50 +/− 1.95 |
| 1 | 11.81 +/− 0.87 |
| 10 | 8.73 +/− 1.96 |

Our results suggest that *Centella* extracts have the ability to inhibit NO production, indicating an inhibition of nitric oxide synthase (NOS) activity. Inhibition of NOS activity has been associated with increased production of IL-1 R antagonist, increased proteoglycan synthesis, increased collagen synthesis and reduction in MMP activity in cartilage. Decrease in protease levels will be beneficial for the joint due to the ability of the cell to now accumulate matrix leading to the overall health of the joint.

EXAMPLE 4

*Centella* Extracts have No Effect on Cell Viability

The effect of *Centella* extracts on the viability of bovine ARC was assessed by the Lactate Dehydrogenase Assay (LDH). Bovine ARC was set up for experiments as outlined in Example 2. The medium collected was then used for analysis of LDH levels. Lactate dehydrogenase is an enzyme that is released into the medium from dead cells and is used to assess cytotoxicity of compounds.

Table-4 shows the LDH optical density as a result of concentration of *Centella* extract added to the cell medium.

TABLE 4

Effect of *Centella* extracts on cell viability

| Centella extract (micrograms/milliliter) | LDH (Optical Density) |
|---|---|
| 0 | 0.33 +/− 0.06 |
| 1 | 0.19 +/− 0.01 |
| 10 | 0.18 +/− 0.03 |

Our results show that *Centella* extracts do not affect the viability of the cells, indicating the *centella* extracts would not in any way affect the viability of the cells within the joint.

Although this invention has been shown and described with respect to detailed embodiments thereof, it will be understood by those skilled in the art that various changes in form and detail thereof may be made without departing from the spirit and scope of the claimed invention.

What is claimed is:

1. A method of treating mammalian articular cartilage disorders, said method comprising:
   parenterally administering a therapeutically effective amount of a parenteral composition, said composition comprising:
   between about 0.001% to about 1% by weight of an extract of *Centella* comprising asiatic acid, madecassic acid, and asiaticoside and a parenterally acceptable carrier,
   wherein the composition is administered to an affected site having mammalian articular cartilage disorder.

2. The method of claim 1, wherein the articular cartilage disorder is selected from the group consisting of arthritis, osteoarthritis, inflammatory joint disease, trauma related cartilage injury, and degenerative disc disease.

3. The method of claim 1, wherein the carrier is selected from the group consisting of sterile water, sterile saline solution, albumin, gelatin, collagen, polysaccharide, monosaccharides, polyvinylpyrrolidone, polylactic acid, polyglycolic acid, polymeric amino acids, fixed oils, ethyl oleate, liposomes, glucose, sucrose, lactose, mannose, dextrose, dextran, cellulose, mannitol, sorbitol, polyethylene glycol, isopropyl alcohol, gaseous fluorocarbons, ethyl alcohol, polyvinyl pyrrolidone, propylene glycol, glycerine, gel-producing material, stearyl alcohol, stearic acid, spermaceti, sorbitan monooleate, and methylcellulose.

4. The method of claim 1, wherein the carrier comprises a colloidal dispersion system.

5. The method of claim 4, wherein the colloidal dispersion system comprises a system selected from the group consisting of nanocapsules, microspheres, beads, lipid-based systems, oil-in-water emulsions, micelles, mixed micelles, and liposomes.

6. The method of claim 1, wherein the carrier comprises a carrier selected from the group consisting of biodegradable hydrogel matrices, dendritic polymer conjugates, hyaluronic acid, and multivesicular liposomes.

7. The method of claim 1, wherein the composition also contains a solubilizing compound.

8. The method of claim 7, wherein the solubilizing compound is an amino acid compound selected from the group consisting of alanine, arginine, aspartic acid, asparagine, cysteine, glutamic acid, glutamine, glycine, histidine, leucine, isoleucine, lysine, methionine, phenylalanine, proline, serine, threonine, tryptophan, tyrosine, and valine.

9. The method of claim 1, wherein the parenteral administration is selected from the group consisting of intra-articularly, intracisternally, intraocularly, intraventricularly, intrathecally, intravenously, intramuscularly, intra-peritoneally, intradermally, and intratracheally.

10. The method of claim 1, wherein the parenteral administration is intra-articularly into the synovial tissues.

11. The method of claim 1, wherein the parenteral administration is delivered intermittently.

12. The method of claim 1, wherein the parenteral administration is delivered continuously.

* * * * *